(12) United States Patent
Giulianotti et al.

(10) Patent No.: US 10,105,272 B2
(45) Date of Patent: Oct. 23, 2018

(54) PATIENT HOLDING HOSPITAL UNIT, PATIENT TRANSPORTATION SYSTEM AND PATIENT TRANSPORTATION AND LIFE SUPPORT SYSTEM

(71) Applicant: THE BOARD OF TRUSTEES OF THE UNIVERSITY OF ILLINOIS, Urbana, IL (US)

(72) Inventors: Pier Giulianotti, Urbana, IL (US); Arturo Vittori, Urbana, IL (US); Andreas Vogler, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 251 days.

(21) Appl. No.: 14/897,638

(22) PCT Filed: Jun. 13, 2014

(86) PCT No.: PCT/US2014/042277
§ 371 (c)(1),
(2) Date: Dec. 10, 2015

(87) PCT Pub. No.: WO2014/201334
PCT Pub. Date: Dec. 18, 2014

(65) Prior Publication Data
US 2016/0120723 A1 May 5, 2016

Related U.S. Application Data
(60) Provisional application No. 61/834,511, filed on Jun. 13, 2013.

(51) Int. Cl.
*A61G 10/00* (2006.01)
*A61G 13/08* (2006.01)
(Continued)

(52) U.S. Cl.
CPC .......... *A61G 10/005* (2013.01); *A61G 13/08* (2013.01); *A61G 13/104* (2013.01);
(Continued)

(58) Field of Classification Search
CPC ................. A61M 16/20; A61G 10/005; A61G 11/00–11/009; A61G 12/001; A61G 12/008; A61G 12/105; A61G 2203/22
See application file for complete search history.

(56) References Cited

U.S. PATENT DOCUMENTS

| 2,742,900 A | 4/1956 | Giorgio et al. |
| 3,239,843 A | 3/1966 | Lobelle |

(Continued)

FOREIGN PATENT DOCUMENTS

| CN | 203168090 | 9/2013 |
| GB | 828731 A | 2/1960 |

(Continued)

OTHER PUBLICATIONS

Corrected International Preliminary Report on Patentability for International Application No. PCT/US2014/042279 filed Jun. 13, 2014 on behalf of The Board of Trustees of the University of Illinois, dated Jan. 29, 2016.

(Continued)

*Primary Examiner* — Thaddeus Cox
(74) *Attorney, Agent, or Firm* — Steinfl + Bruno, LLP

(57) ABSTRACT

A patient holding hospital unit is described. The patient holding hospital unit has a supporting surface configured to receive a patient and a life support system. The supporting surface has a container restrained to the supporting surface that contains an anesthesia machine, reservoirs and related ducts, perfusion devices, an automatic control system, a power supply unit, a power supply line. The container also has dispensing valves arranged on an external surface of the
(Continued)

container together with a control interface and the supply valves and electric connector of the power supply line are arranged at a connecting member adapted to be mounted to a base member configured to supply gases under pressure to the reservoirs and power to the control system.

19 Claims, 14 Drawing Sheets

(51) Int. Cl.
*A61M 5/168* (2006.01)
*A61M 16/01* (2006.01)
*A61M 16/20* (2006.01)
*A61G 13/10* (2006.01)

(52) U.S. Cl.
CPC ........... *A61G 13/107* (2013.01); *A61M 5/168* (2013.01); *A61M 16/01* (2013.01); *A61M 16/20* (2013.01); *A61G 13/102* (2013.01); *A61G 2203/22* (2013.01); *A61G 2203/80* (2013.01)

(56) References Cited

U.S. PATENT DOCUMENTS

| | | | |
|---|---|---|---|
| 3,783,863 A | 1/1974 | Kliever | |
| 4,750,474 A * | 6/1988 | Dukhan | A61G 11/00 128/205.26 |
| 5,322,245 A | 6/1994 | Bassick | |
| 5,626,151 A | 5/1997 | Linden | |
| 5,975,081 A | 11/1999 | Hood et al. | |
| 6,047,203 A | 4/2000 | Sackner et al. | |
| 6,073,284 A | 6/2000 | Borders | |
| 6,112,333 A | 9/2000 | Mazzei | |
| 6,155,260 A | 12/2000 | Lavin et al. | |
| 6,245,028 B1 | 6/2001 | Furst et al. | |
| 6,321,764 B1 * | 11/2001 | Gauger | A61G 10/005 135/128 |
| 6,401,278 B1 | 6/2002 | Hayes et al. | |
| 6,460,187 B1 | 10/2002 | Siegel | |
| 6,493,890 B2 | 12/2002 | Smeed | |
| 6,792,623 B2 | 9/2004 | Luppi | |
| 7,296,570 B2 | 11/2007 | Hutchinson | |
| 8,033,281 B2 | 10/2011 | Kneale et al. | |
| 2002/0138905 A1 | 10/2002 | Bartlett et al. | |
| 2003/0097060 A1 | 5/2003 | Yanof et al. | |
| 2004/0040064 A1 | 3/2004 | Mah et al. | |
| 2004/0267145 A1 | 12/2004 | David et al. | |
| 2006/0150335 A1 | 7/2006 | Dankbaar et al. | |
| 2009/0235928 A1 | 9/2009 | Borsari | |
| 2010/0031443 A1 | 2/2010 | Georgiev et al. | |
| 2010/0162488 A1 * | 7/2010 | Dahlin | A61B 6/04 5/600 |
| 2010/0242150 A1 | 9/2010 | Trouillot | |
| 2011/0076771 A1 | 3/2011 | Gabriele et al. | |
| 2011/0289644 A1 | 12/2011 | Beshlian | |
| 2012/0136231 A1 | 5/2012 | Markel | |
| 2012/0146784 A1 | 6/2012 | Hines et al. | |
| 2012/0158074 A1 | 6/2012 | Hall | |
| 2012/0246795 A1 | 10/2012 | Scheffler et al. | |
| 2013/0085510 A1 | 4/2013 | Stefanchik et al. | |
| 2013/0178870 A1 | 7/2013 | Schena | |

FOREIGN PATENT DOCUMENTS

| | | |
|---|---|---|
| JP | 2006280534 | 10/2006 |
| JP | 2007175266 | 7/2007 |
| KR | 10-2011-030038 A | 3/2011 |
| WO | 1992/18084 A1 | 10/1992 |
| WO | 1999/029235 A | 6/1999 |
| WO | 0000152 | 1/2000 |
| WO | 03/097145 | 11/2003 |
| WO | 2005/102084 A1 | 11/2005 |
| WO | 2007/128571 | 11/2007 |

OTHER PUBLICATIONS

International Preliminary Report on Patentability for PCT/2014/042279 filed Jun. 13, 2014 on behalf of The Board of Trustees of the University of Illinois, dated Dec. 4, 2015.
International Preliminary Report on Patentability for PCT/2014/042277 filed Jun. 13, 2014 on behalf of The Board of Trustees of the University of Illinois, dated Dec. 15, 2015.
International Search Report for PCT/US2014/042279 filed Jun. 13, 2014 on behalf of The Board of Trustees of the University of Illinois, dated Nov. 4, 2014.
Written Opinion for PCT/U52014/042279 filed Jun. 13, 2014 on behalf of The Board of Trustees of the University of Illinois, dated Nov. 4, 2014.
International Search Report for PCT/US2014/042286 filed Jun. 13, 2014 on behalf of The Board of Trustees of the University of Illinois, dated Nov. 4, 2014.
Written Opinion for PCT/US2014/042286 filed Jun. 13, 2014 on behalf of The Board of Trustees of the University of Illinois, dated Nov. 4, 2014.
International Preliminary Report on Patentability for PCT/US2014/042286 filed Jun. 13, 2014 on behalf of The Board of Trustees of the University of Illinois, dated Nov. 30, 2015.
International Search Report and Written Opinion for PCT/US2014/042277 filed Jun. 13, 2014 on behalf of The Board of Trustees of the University of Illinois, dated Nov. 7, 2014.
International Search Report and Written Opinion for PCT/US2014/042281 filed Jun. 13, 2014 on behalf of The Board of Trustees of the University of Illinois, dated Oct. 20, 2014.
International Preliminary Report on Patentability for PCT/US2014/042281 filed Jun. 13, 2014 on behalf of The Board of Trustees of the University of Illinois, dated Jun. 26, 2015.

* cited by examiner

A

B

C

D

E

PATIENT HOLDING HOSPITAL UNIT, PATIENT TRANSPORTATION SYSTEM AND PATIENT TRANSPORTATION AND LIFE SUPPORT SYSTEM

CROSS REFERENCE TO RELATED APPLICATIONS

The present application is the national stage entry of International Application No. PCT/US2014/042277, filed on Jun. 13, 2014, which claims priority to U.S. Provisional Application 61/834,511 filed on Jun. 13, 2013, which is incorporated herein by reference in its entirety.

FIELD

This present disclosure relates to a patient holding hospital unit equipped with appliances for supporting life of a patient laying thereon, that may be enclosed in a protective cocoon supported by a robotic movement system for transporting surgical patients to and from an operating room.

BACKGROUND

The movement of a surgery patient from his hospital room to anesthesia, to the surgical table and back, involves many people and complicated equipment movement and can be especially cumbersome with the increasing number of obese patients. Up to six people may be needed to lift a patient from one table to another. One or two people are involved moving the patient and life support equipment within the hospital.

The PCT publication no. WO00/00152 discloses a bed having a patient support surface removably placed on support arms of a support assembly, on its turn coupled to a base with wheels. This bed may be useful for transporting a patient in a hospital, though the patient support surface must be detached from the support assembly and lifted by at least two persons to displace the patient on a surgical table or on a bed.

Outside the operating room, the quality of the sterile environment is often difficult to control.

The Japanese Patent application no. JP 2007175266 discloses a patient transportation device having a bed on which a patient lies and a capsule which covers the bed, that may be used for transporting with an aircraft a patient, to be kept in a protected space, while preventing leakage of contaminated air.

The documents WO 92/18084 and JP2006280534 disclose chambers adapted to house a patient laying on a bed, having inlet and outlet openings for transporting gases into the chamber and to or from the patient in the chamber.

Therefore, there is an unmet need to apply modern robotic technologies to benefit the patient under anesthesia while increasing comfort and safety.

SUMMARY

The above needs are met by a patient holding hospital unit, comprising:
 a supporting surface configured to receive a patient; and
 a life support system restrained to the supporting surface, the system comprising:
  an anesthesia machine;
  a plurality of reservoirs suitable to contain gases under pressure;
  a first set of gas supply ducts respectively connected to outlet ports of the reservoirs, the free ends of the gas supply ducts being provided with respective dispensing valves;
  a second set of gas supply ducts respectively connected to inlet ports of the reservoirs, the free ends of the gas supply ducts being provided with respective supply valves;
  one or more perfusion devices;
  an automatic control system operably connected to the anesthesia machine, dispensing valves, perfusion devices and provided with a control interface;
  a power supply unit operably connected to the automatic control system; and
  a power supply line operably connected to the automatic control system in parallel relative to the power supply unit, the power supply line having an electric connector,
 wherein the anesthesia machine, reservoirs and related ducts, perfusion devices, automatic control system, power supply unit and power supply line are arranged in a container restrained to the patient supporting surface, and
 wherein the dispensing valves are arranged on an external surface of the container together with the control interface and the supply valves and electric connector of the power supply line are arranged at a connecting member adapted to be mounted to a base member configured to supply gases under pressure to the reservoirs and power to the control system.

The patient holding hospital unit may be equipped with a computerized system configured to monitor, to control and to adapt functions performed by the appliances of the life support system in order to preserve patient's vital functions.

In one embodiment of the present disclosure, the embodiment provides a patient transportation system, comprising:
 a robotic movement system including a motorized trolley and a substantially horizontal fork-shaped support having two substantially parallel cantilever beams separated by a gap; and
 a protective cocoon having a substantially cylindrical shape and defining an enclosed tubular space adapted to house a patient laying on a supporting surface, the cocoon, comprising:
  a lower shell having a substantially half-cylinder shape with an opening in correspondence of the gap of the fork-shaped support,
  an upper shell having a substantially half-cylinder shape coaxially hinged to the lower shell so as to slide over the lower shell by rotating around their common axis, the upper shell being adapted to form with the lower shell a tubular space having only an opening at one end through which a supporting surface with a patient laying thereon may be inserted,
  a base support adapted to be laid upon the fork-shaped support and to sustain the lower shell, defining a substantially cylindrical surface having a bottom hatch in correspondence of the gap of the fork-shaped support, and
  at least one door hinged to the base support and adapted to close the opening of the tubular space.

In one embodiment, the robotic movement system is be equipped with an electric motor for moving the patient transportation system, with electric accumulators coupled to power the electric motor and a control system configured to command the electric motor.

In one embodiment of the present disclosure, the embodiment provides a patient holding hospital system that may be easily connected to/disconnected from a e.g. ground post, more generally a docking post, mount and the like, located in an operating room or in a hospital room and comprising:

a surgical table defining a patient supporting surface and having fasteners of a first set installed on the opposite side of the patient supporting surface;

a T-shaped connecting member or docking port having:
 a top portion having fasteners of a second set adapted to engage in a detachable manner with the fasteners of the first set to hold firmly the surgical table,
 a bottom portion having fasteners and connectors of a third set adapted to engage in a detachable manner with upper fasteners and connectors of a post, mount or similar docking member located in an operating room or in a hospital room, e.g. a docking member of a surgical station, and to keep firmly the T-shaped connecting member to the mount,
 at least one side portion having fasteners and connectors of a fourth set, and
 internal conduits and at least an electric cable joining together corresponding connectors of the third set and of the fourth set; and a life support system, having:
 holding fasteners adapted to engage in a detachable manner with the fasteners of the fourth set and to keep firmly the life support system to the T-shaped connecting member,
 inlet gas connectors and at least an input electric connector configured to couple in a detachable manner with corresponding connectors of the fourth set,
 outlet gas connectors adapted to couple with external tubes for delivering oxygen and/or an anesthetic gas, and
 electrically operated devices for supporting life of a patient laying on the surgical table, configured to be powered through the input electric connector and having inlet gas conduits coupled with the inlet gas connectors and outlet gas conduits coupled with the outlet gas connectors.

Additional non-limiting features, embodiments and aspects of the present disclosure are described in the ensuing description.

The claims as filed are integral part of this specification and are herein incorporated by reference.

DETAILED DESCRIPTION

Figure 1:
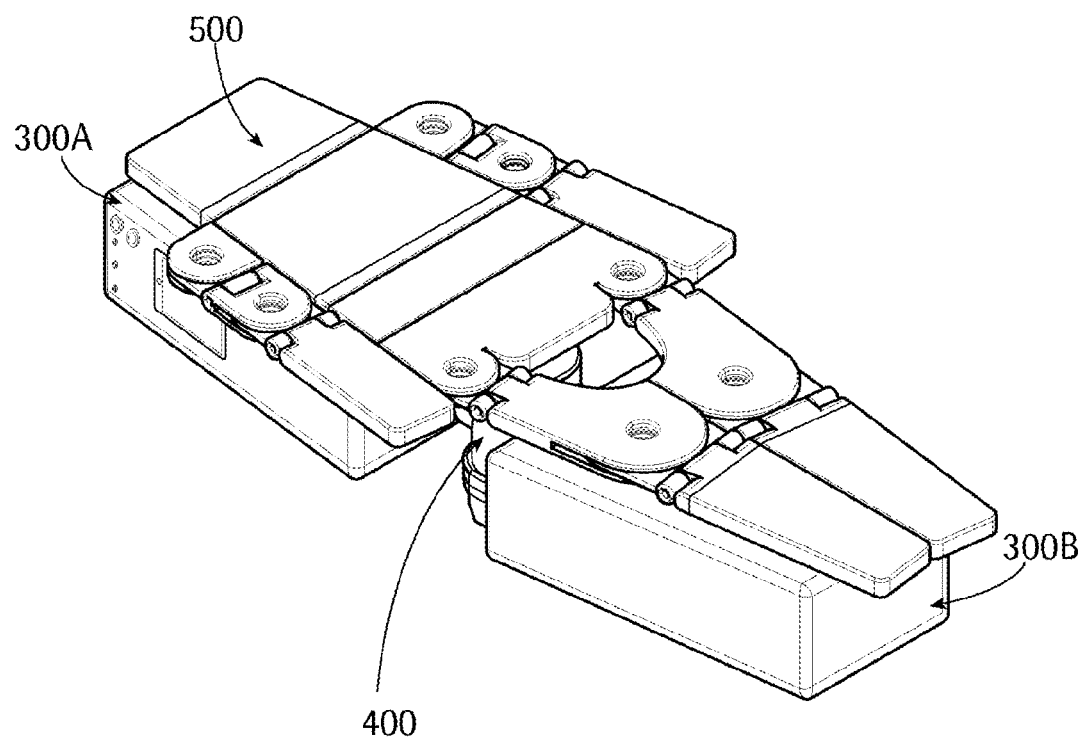
FIG. 1 shows a perspective view of a patient holding hospital unit constructed, in accordance with an embodiment of the present disclosure.
Figure 2:
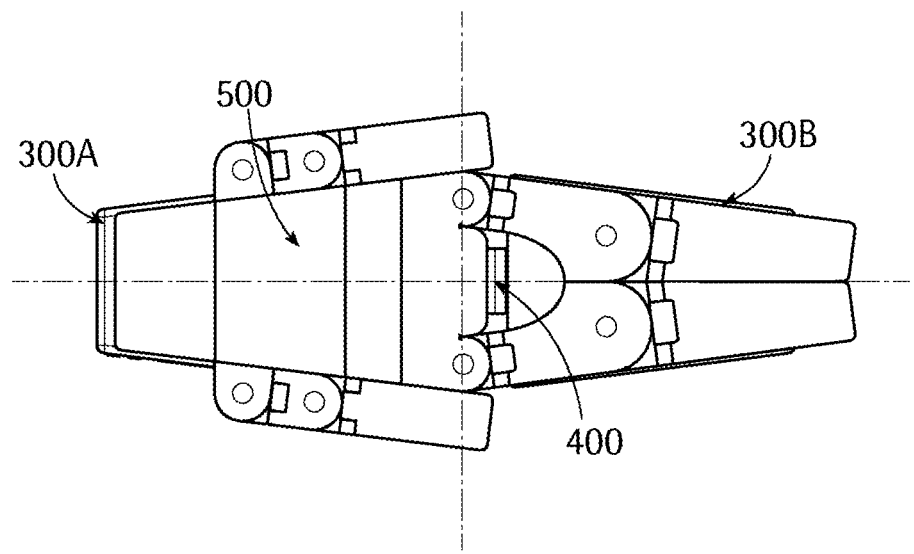
FIGS. 2-4 show plan, front and side views, respectively, of the patient holding hospital unit of FIG. 1.
Figure 3:
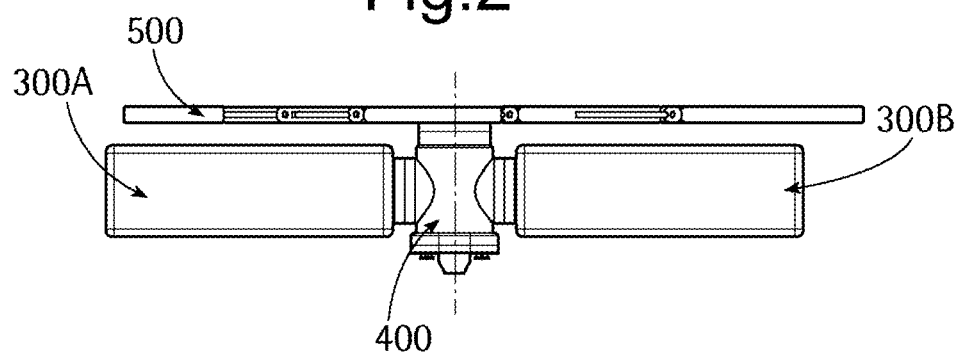
Figure 4:
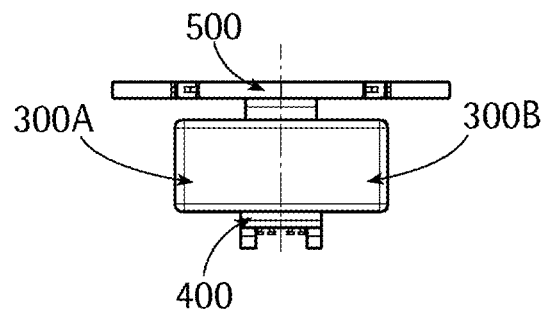

A patient holding hospital unit according to an embodiment of the present disclosure is shown in the perspective view of FIG. 1 and in the plan, front and side views of FIGS. 2-4, respectively. It comprises a supporting surface 500, that may also constitute a surgical table, and a life support system, that in the shown example is modularly composed of two boxes 300A and 300B, restrained to the supporting surface 500. The patient holding hospital unit has a modular structure and the modules, i.e. the supporting surface 500 and the boxes 300A and 300B, may be attached/detached one from the other and may possibly be used separately, as it will be better explained hereinafter.

The supporting surface 500 is preferably composed of a plurality of individually movable portions hinged together and movable one in respect to the other so as to define a chair or a bed or to place the laying patient in one out of a large number of possible positions. For example, the supporting surface 500 comprises individually movable arms and leg portions that can be pivoted relative to the bed frame about respective horizontal axes parallel to the bed frame and to vertical axes perpendicular thereto. The supporting surface 500 may advantageously be provided with integrated actuators allowing to selectively move these portions. Such actuators may e.g. be electromechanical or hydraulic actuators.

The supporting surface 500 of the patient holding hospital unit is sustained by a T-shaped connecting member 400, to which the life support system 300 is connected. The life support system has a modular structure and may be composed of two boxes 300A and 300B containing different appliances for supporting patient's life, as shown by way of example in FIGS. 1-4, or by a single box or even three or more boxes. The life support system is modular and may be adapted according to the needs by adding/removing one or more boxes in order to provide only the appliances that are really needed for supporting patient's life.

Figure 5:
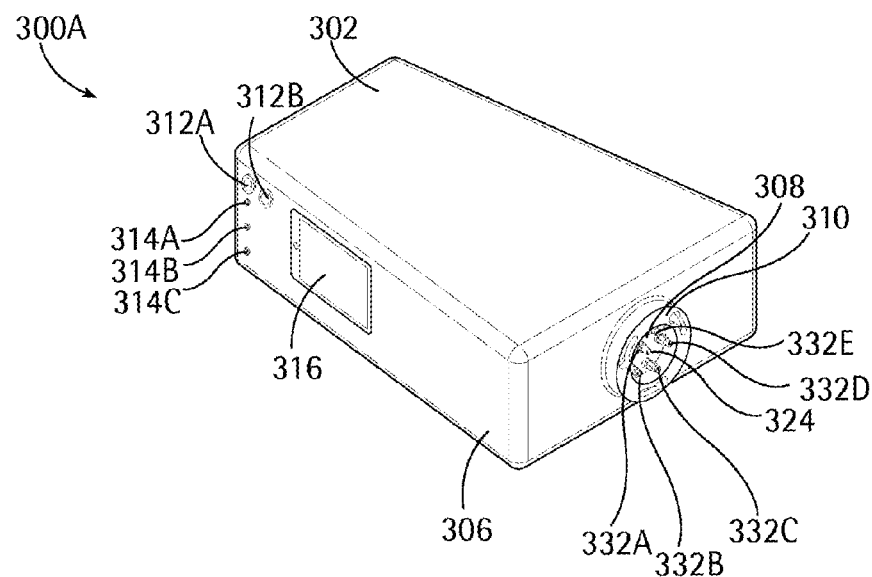
FIGS. 5-7 show a life support system destined to be restrained to the supporting surface of the patient holding hospital unit according to an embodiment of the present disclosure.
Figure 6:
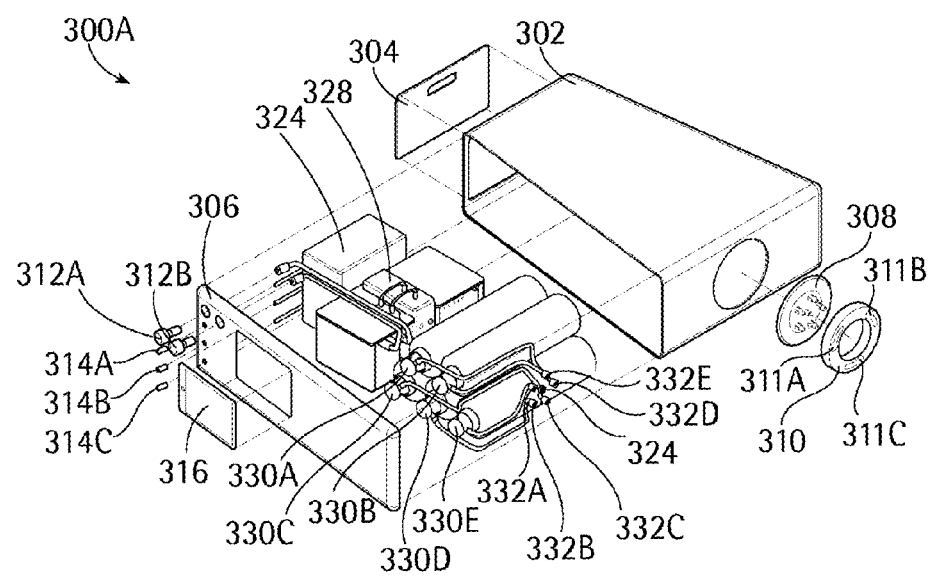
Figure 7:
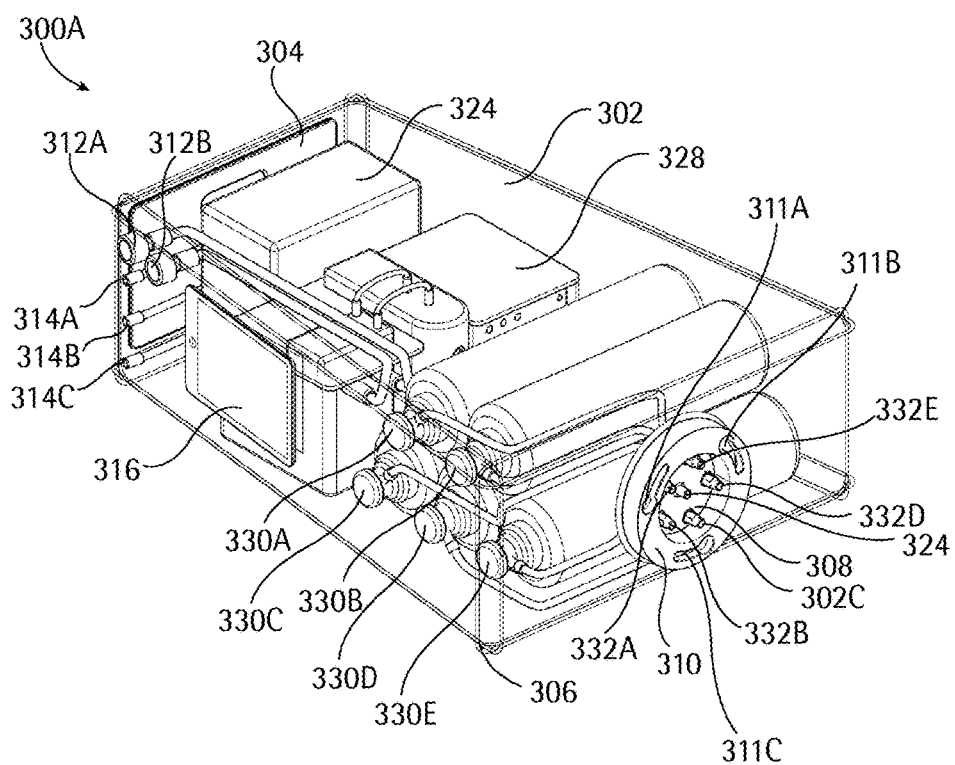
Figure 8:
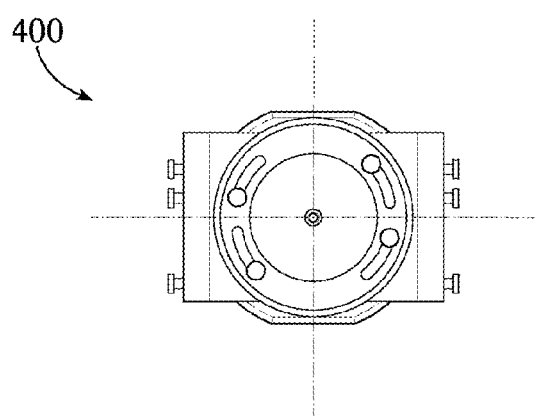
FIGS. 8-11 show a T-shaped connecting member for sustaining a surgical table of a patient holding hospital unit according to an embodiment of the present disclosure.
Figure 9:
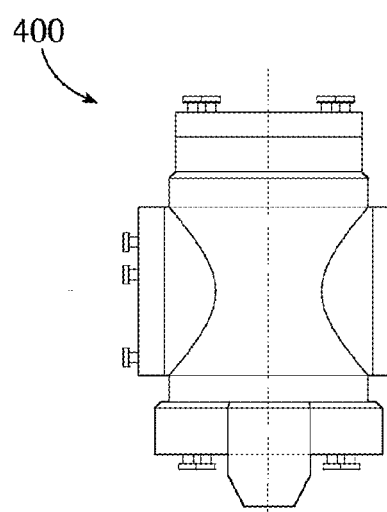
Figure 10:
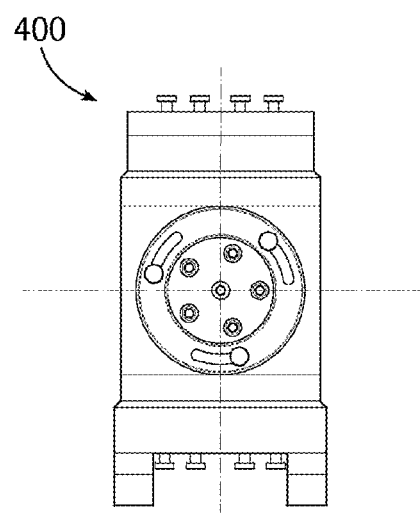
Figure 11:
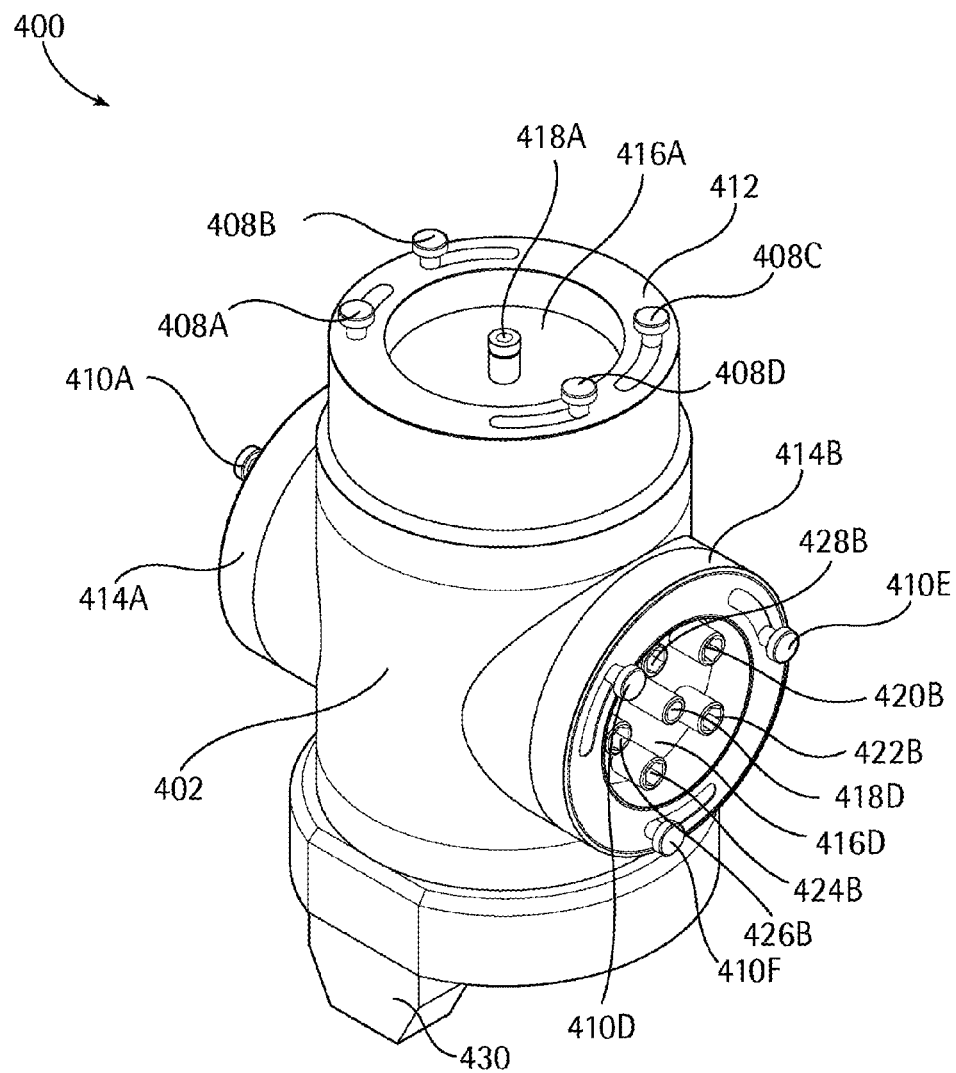

An embodiment of a full comprehensive box 300A of the life support system is shown by way of example in FIGS. 5-7, in which the reference numerals have the following meaning:

| | |
|---|---|
| 302 | MAIN BOX |
| 304 | BACK DOOR BOX |
| 306 | SIDE DOOR BOX |
| 308 | BASE CONNECTOR |
| 310 | FLANGE CONNECTOR |
| 311A, B, C | SUPPORT CONNECTOR |
| 312A | INPUT OXYGEN CONNECTOR A |
| 312B | OUTPUT OXYGEN CONNECTOR B |
| 314A, B, C | INFUSION CONNECTOR OUTPUT |
| 316 | MONITOR |
| 324 | INFUSION MACHINE |
| 326A, B, C | INFUSION SYRINGE A |
| 328 | ANAESTHESIA MACHINE |
| 330A | GAS TANK OXYGEN |
| 330B | GAS TANK VACUUM |
| 330C | GAS TANK NITROUS |
| 330D | GAS TANK MEDICAL |
| 330E | GAS TANK NITROGEN |
| 332A | CONNECTOR GAS TANK OXYGEN |
| 332B | CONNECTOR GAS TANK VACUUM |
| 332C | CONNECTOR GAS TANK NITROUS |
| 332D | CONNECTOR GAS TANK MEDICAL |
| 332E | CONNECTOR GAS TANK NITROGEN |
| 324 | ELECTRICAL CONNECTOR |

Of course, it is not necessary to enclose in a single box all life support appliance. For example, a box of the life support system may contain only tanks of anesthetic gas and another box may contain only oxygen tanks. With this arrangement, when an anesthetized patient is not to be kept under anesthesia any longer but still needs a respiration support, it is possible to adapt the life support system by removing the box containing the tanks of anesthetic gas and to leave the box containing the oxygen tanks.

In the shown embodiment the box has supporting connectors 311 to the T-shaped connecting member 400, inlet and outlet gas connectors 312A and 312B, 322A, 322B, 322C, 322D, 322E, and at least an electric connector 324. In practice the box(es) 300 constitute a portable life support system destined to follow the patient laying on the supporting surface to keep him alive.

In general, a box of the life support system may include appliances for supporting life of patients, such as for example an anesthesia machine, a plurality of reservoirs suitable to contain gases under pressure, a first set of gas supply ducts respectively connected to outlet ports of the reservoirs, the free ends of the gas supply ducts being provided with respective dispensing valves, a second set of gas supply ducts respectively connected to inlet ports of the reservoirs, the free ends of the gas supply ducts being provided with respective supply valves, one or more perfusion devices, an automatic control system operably connected to the anesthesia machine, dispensing valves, perfusion devices and provided with a control interface, a power supply unit operably connected to the automatic control system, a power supply line operably connected to the automatic control system in parallel relative to the power supply unit, the power supply line having an electric connector. The anesthesia machine, reservoirs and related ducts, perfusion devices, automatic control system, power supply unit and power supply line are all arranged in the container 300A (or 300B) restrained to the patient supporting surface. The dispensing valves are arranged on an external surface of the container together with the control interface and the supply valves and electric connector of the power supply line are arranged at a connecting member adapted to be mounted to a base member configured to supply gases under pressure to the reservoirs and power to the control system.

According to an embodiment, the appliances contained in the box 300A(B) have a control circuit configured to determine whether the T-shaped connecting member 400 is connected on a ground post in an operating room, in order to decide whether oxygen and/or anesthetic gas should be provided to the patient laying on the supporting surface 500 by the tanks contained in the box 300A(B), or the tanks may be bypassed because the patient is in an operating room and life support is provided through other ways.

An exemplary embodiment of a T-shaped connecting member 400 is shown in FIGS. 8-11, wherein the reference numerals have the following meaning:

| | |
|---|---|
| 402 | CENTRAL PART |
| 404 | TOP PART |
| 406A, B, C, D | ACTUATORS QUARTER-TURN HOOKS |
| 408A, B, C, D | QUADRUPLE QUARTER-TURN HOOKS |
| 409A, B, C, D | QUADRUPLE QUARTER-TURN HOOKS |
| 410A, B, C, D, E, F | POST |
| 412 | TOP FLANGE |
| 414A, B | LATERAL FLANGE |
| 416A, B, C, D | PLATE CONNECTOR |
| 418A, B, C, D | ELECTRICAL CONNECTOR |
| 420A, B, C | OXYGEN CONNECTOR |
| 422A, B, C | VACUUM CONNECTOR |
| 424A, B, C | NITROUS OXIDE CONNECTOR |
| 426A, B, C | MEDICAL AIR CONNECTOR |
| 428A, B, C | NITROGEN CONNECTOR |
| 430 | FLANGE BASE LIFTING |

The T-shaped connecting member 400 allows to sustain in a detachable manner the supporting surface 500 and the box(es) of the life support system and, allows to mount the patient holding hospital unit on a ground post, mount or more generally a docking post or member located in an operating or hospital room. Substantially, the T-shaped connecting member 400 comprises a top portion having fasteners of a second set adapted to engage in a detachable manner with the fasteners of the first set to hold firmly the surgical table, a bottom portion having fasteners and connectors of a third set adapted to engage in a detachable manner with upper fasteners and connectors of a mount of a surgical station and to keep firmly the T-shaped connecting member to the mount, at least one side portion having fasteners and connectors of a fourth set, and internal conduits and at least an electric cable joining together corresponding connectors of the third set and of the fourth set. If more than one box of the life support system is to be connected, the T-shaped connecting member 400 will be equipped with at least two or more identical side portions with fasteners and connectors.

Figure 12:
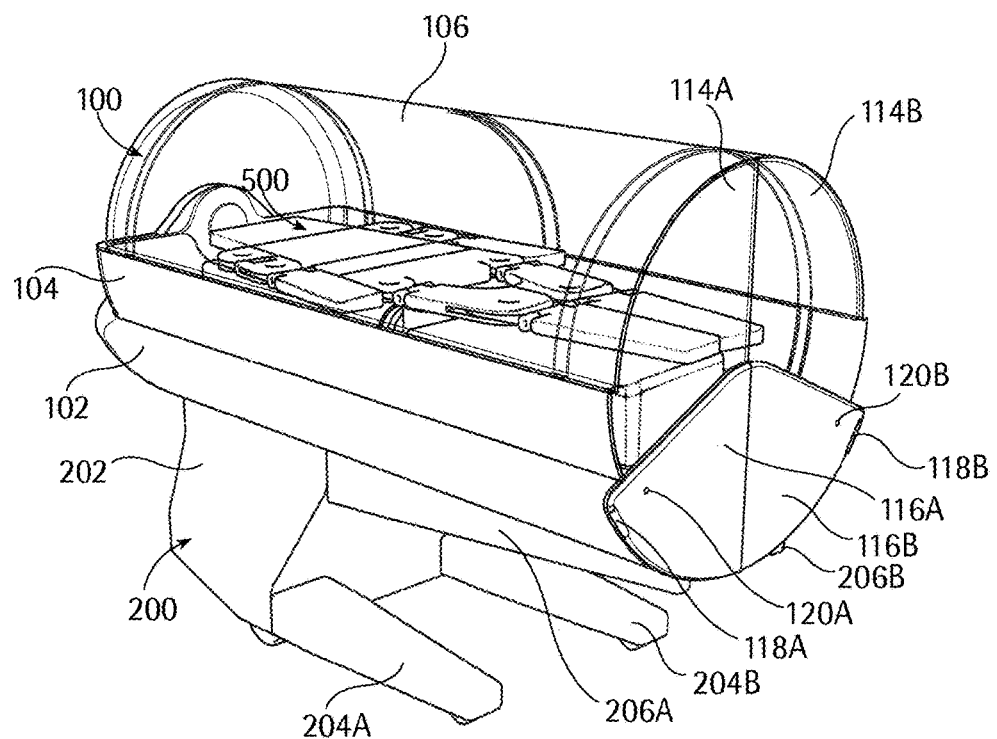
FIG. 12 shows a perspective view taken from the patient's right side of the patient transportation and life support system constructed in accordance with an embodiment of the present disclosure.
Figure 13:
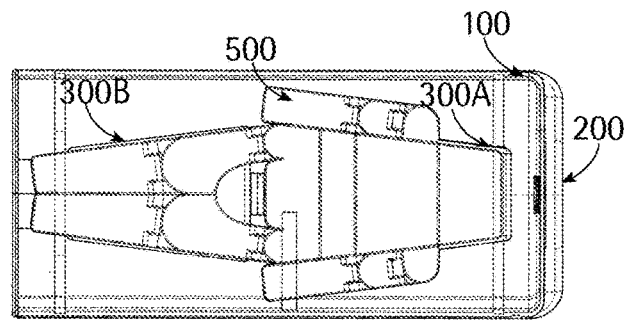
FIGS. 13-16 depict an embodiment of a robotically driven transportation system according to an embodiment of the present disclosure containing a patient holding hospital unit.
Figure 14:
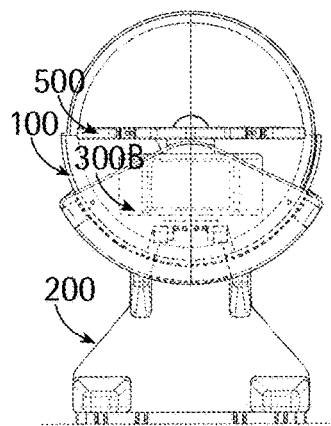
Figure 15:
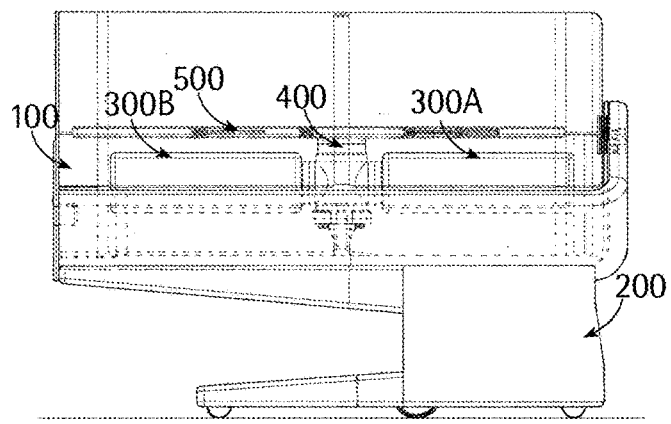
Figure 16:
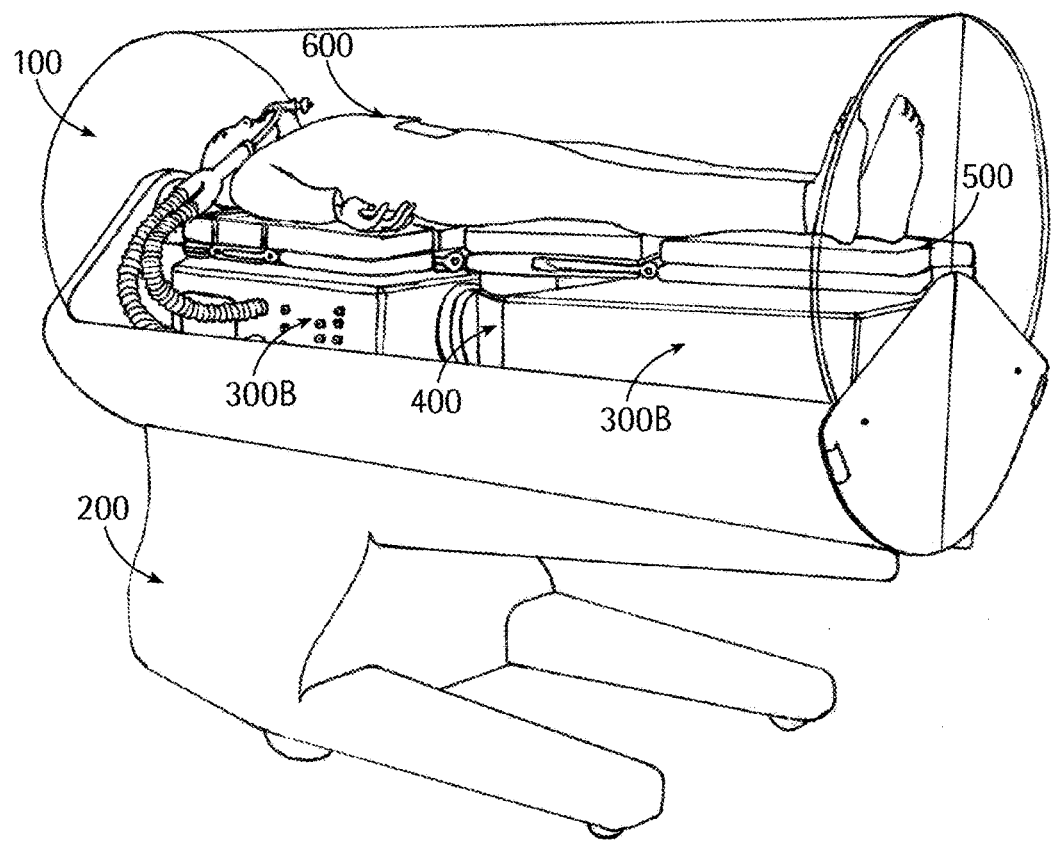
Figure 17:
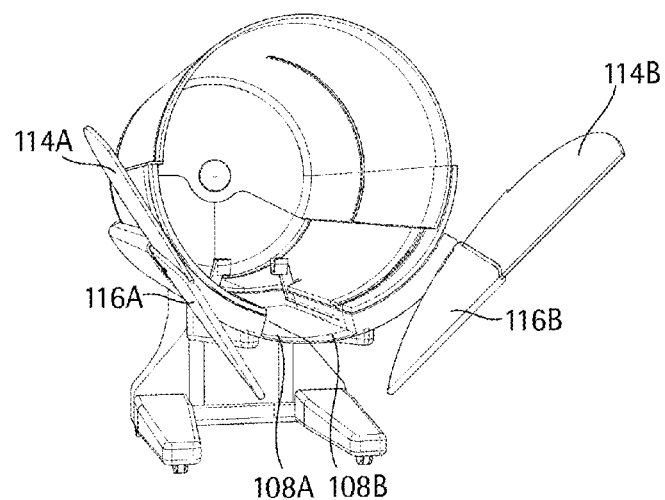
FIG. 17 shows a robotically driven transportation system of FIGS. 13-16 with front doors open and bottom hatch closed.
Figures 18, 19:
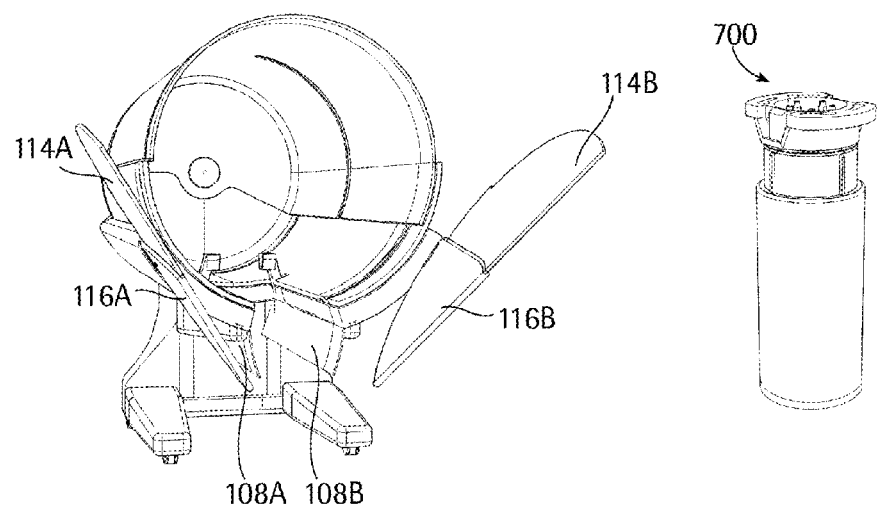
FIG. 18 shows a robotically driven transportation system of FIG. 16 with front doors and bottom hatch open.
FIG. 19 shows a ground post 700, which serves as a stationary fixation for the patient holding hospital unit according to an embodiment of the present disclosure.
Figure 20A:
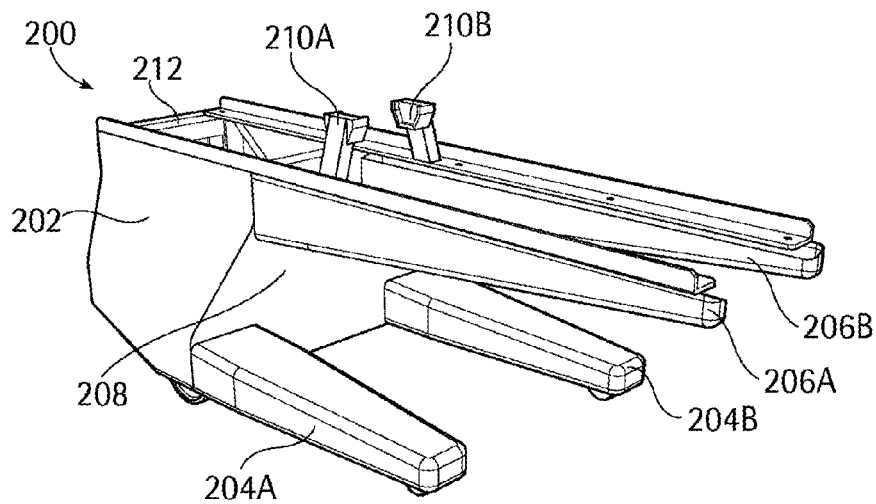
FIGS. 20A and 20B are views of the support of the enclosing cocoon of the robotically driven transportation system shown in FIGS. 13-16.
Figure 20B:
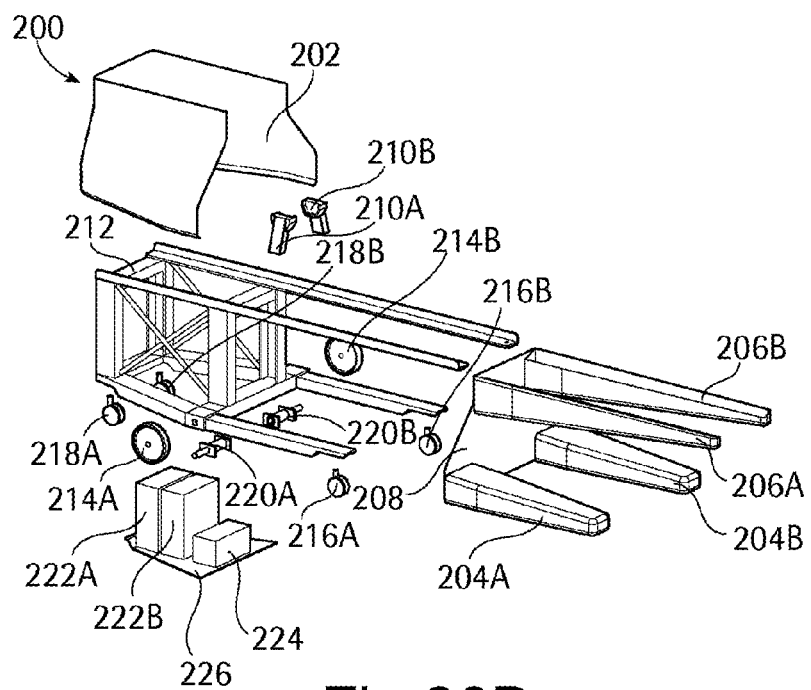
Figure 21A:
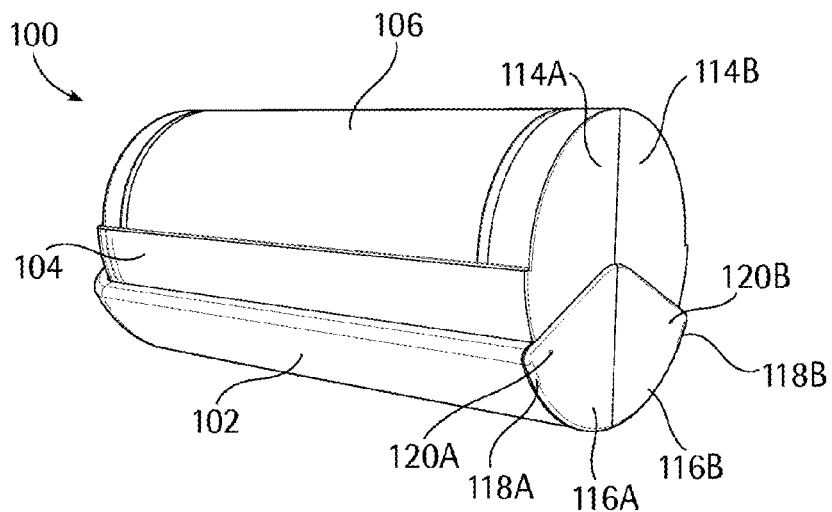
FIGS. 21A and 21B are views of the enclosing cocoon of the robotically driven transportation system of figures from 13 to 16.
Figure 21B:
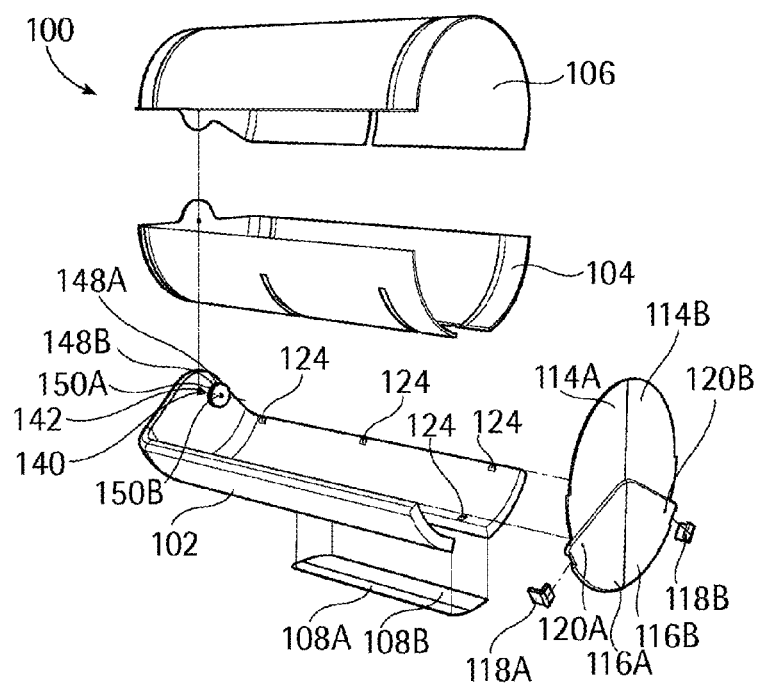

When the patient is in the operating room, the patient holding hospital unit is fixed upon a ground post, that may be for example of the type shown in FIG. 19. When the patient laying on the patient holding hospital unit is to be transported from the operating room to another room of the hospital, the patient holding hospital system is to be detached from the g round post 700 and connected to a transportation system, for example the transportation system an exemplary embodiment of which is depicted in FIGS. 13-18, to form the patient transportation and life support system of FIG. 12. The shown patient transportation system substantially comprises a robotic movement system including a motorized trolley 200 and a substantially horizontal fork-shaped support having two substantially parallel cantilever beams separated by a gap, and a protective cocoon 100 having a substantially cylindrical shape and defining an enclosed tubular space adapted to house a patient laying on a supporting surface. The cocoon comprises a lower shell 104 having a substantially half-cylinder shape with an opening in correspondence of the gap of the fork-shaped support, an upper shell 106 having a substantially half-cylinder shape coaxially hinged to said lower shell 104 so as to slide over the lower shell 104 by rotating around their common axis, the upper shell 106 being adapted to form with the lower shell 104 a tubular space having only an opening at one end through which a supporting surface with a patient laying thereon may be inserted, a base support 102 adapted to be laid upon the fork-shaped support and to sustain said lower shell 104, defining a substantially cylindrical surface having a bottom hatch in correspondence of the gap of the fork-shaped support, and at least one door hinged to said base support 102 and adapted to close said opening of the tubular space.

The patient transportation system conveniently comprises clamping means installed in the tubular space for securing the supporting surface with a patient laying thereon.

It is to be appreciated that also the transportation system, according to an embodiment of the present disclosure, has a modular structure, because the protective cocoon 100 may be separated from the trolley 200 when it is not necessary to keep the patient in an enclosed space. This may be the case for example when the patient is to be awakened and there is no risk of leakage of anesthetic gas.

Detailed views of embodiments of the trolley 200 and of the protective cocoon 100 are depicted in FIGS. 20A, 20B, and 21A, 21B, respectively. The meaning of the reference numerals is summarized in the following table:

| | |
|---|---|
| 102 | CYLINDER ONE |
| 104 | CYLINDER TWO |
| 106 | CYLINDER THREE |
| 108A, B | BOTTOM HATCH |
| 112 | CYLINDER ROTATION MECHANISM |
| 114A, B | FRONT DOORS |
| 116A, B | FRONT DOORS SUPPORT |
| 118A, B | FRONT ACTUATED HINGE |
| 120A, B | LASER OBSTACLE SENSOR |
| 122A, B, C, D, E, F | CYLINDER ROLLING MOTOR (SEE FIG 33) |
| 124 | SUPPORT WHEEL |
| 126A, B | CYLINDER OPENING MOTOR |
| 128A, B | COGWHEEL |
| 130A, B, C, D | SUPPORT CYLINDER OPENING MOTOR |
| 132A, B | CYLINDER OPENING MOTOR AXIS |
| 134A, B | WORMGEAR |
| 136 | CENTRAL AXIS |
| 138 | TOP SUPPORT CENTRAL AXIS |
| 140 | SUPPORT CENTRAL AXIS PART |
| 142 | BEARING CENTRAL AXIS |
| 144 | O-RING CENTRAL CYLINDER TWO |
| 146 | O-RING CENTRAL CYLINDER THREE |
| 148A, B | PLATE CYLINDER TWO |
| 150A, B | PLATE CYLINDER THREE |
| 200 | TROLLEY |
| 202 | MAIN SHROUD |
| 203 | RECHARGE CONNECTION |
| 204A, B | SUPPORT LONGITUDINAL CASE |
| 206A, B | LONGITUDINAL CASE |
| 208 | FRONT CASE |
| 210A, B | LIFTING |
| 212 | STRUCTURE |
| 214A, B | MAIN WHEEL |
| 216A, B | FRONT WHEEL |
| 218A, B | BACK WHEEL |
| 220A, B | WHEEL MOTOR |
| 222A, B | BATTERY |
| 224 | CPU |
| 226 | BASE PLATE |

Figure 22:
FIG. 22 shows A) a surgical table on a ground post configured as a chair; B) a surgical table on a ground post configured as a bed; C) a patient holding hospital unit with a life support system; D) a patient under anesthesia laying on the patient holding hospital unit mounted on a ground post; E) a patient under anesthesia laying on the patient holding hospital unit enclosed in a patient transportation system.
Figure 22:
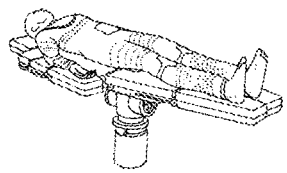
Figure 22:
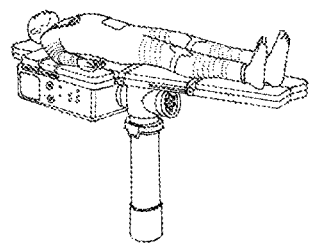
Figure 22:
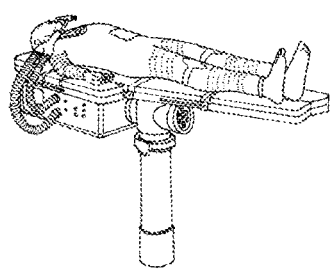
Figure 22:
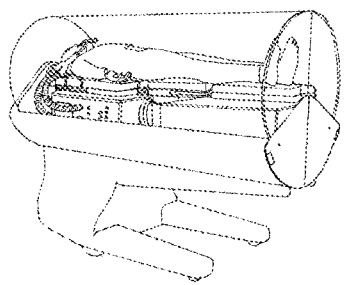

The sequence of images of FIG. 22 from A to E illustrates different operations that may be carried out with a patient transportation and life support system according to an embodiment of the present disclosure. As stated hereinbefore, the surgical table comprises different parts connected one another so as to modify the configuration of the supporting surface 500, for example for configuring it as a chair (A). The patient receives sedation while in the sitting position and then the supporting surface 500 is converted to a flat configuration (B), after which the patient is prepared for surgery (intubation and infusion). The modular life support system is then fixed to the T-shaped connecting member (C) and the patient is connected to the modular life support system (D). The patient holding hospital system is then attached to the robotic movement system and encased in the protective cocoon (E) for transporting the patient to the operating room.

Once in the operating room, the bottom hatch of the protective cocoon is opened and the T-shaped connecting member is fixed to the ground post 700 (FIG. 19). The appliances in the box(es) of the life support system sense that the holding hospital system is connected to the ground post 700 and are bypassed to allow life functions of the patient be supported directly through appliances available in the operating room. Then the supporting surface is detached from the clamping means of the transportation system, that is moved away from the ground post 700.

When the patient laying on the patient holding hospital unit is to be transported from the operating room to another room of the hospital, the front doors 114A, 114B of the protective cocoon 100 are opened (FIG. 17), then also the bottom flaps 108A and 108B, that compose the bottom hatch of the cocoon, are opened (FIG. 18). The whole patient transportation system is moved towards the patient holding hospital system to thread the supporting surface 500 in the protective cocoon 100, then the patient supporting surface 500 is secured to the clamping means of the transportation system and the patient holding hospital unit is detached from the ground post 700. Typically, the supporting surface 500 remains fixed to the T-shaped connecting member 400 to which the life support box(es) is (are) connected, and only the bottom fasteners and connectors of the T-shaped member are detached from the ground post 700 in the operating room. Therefore, the whole patient holding system is fixed to the patient transportation system in order to support life functions while the patient is transported away from the operating room. In this case, the appliances contained in the box(es) 300A (and 300B) are configured to sense whether or not the box is disconnected from the ground post 700, in order to determine respectively whether patient's life functions are to be supported by the appliances or the appliances may be bypassed, because the patient is in the operating room. Finally the front doors of the protective cocoon are closed (FIG. 16) and the patient, whose life functions are supported by the life support system 300, is ready to be moved anywhere in the hospital enclosed in a protective space and without any risk of leakage of gases outside.

The inside of the cocoon is preferably kept under slight overpressure conditions so as to prevent external gases to enter it when the doors are opened and closed.

All these operations may be carried out by a single person without effort even with obese patients, because a patient laying on the supporting surface is always sustained by the ground post and/or by the clamping means of the transportation system.

As an alternative, if a patient does not need life support after a surgical intervention, the box(es) 300A (and 300B) of the life support system and possibly even the T-shaped connecting member 400 may be detached from the supporting surface 500, thus only the supporting surface 500 will be held by the patient transportation system.

In one embodiment, the clamping means of the patient transportation system are mechanically coupled to electric linear actuators fixed to the fork-shaped support and configured to lift the supporting surface 500 attached to the clamping means.

In one embodiment, upper shell and the lower shell of the protective cocoon may slide one in respect to the other in order to have rapid access to the patient in case of emergency. For example, for manual interaction with the patient and/or the life support system, the upper half shell 106 of the cocoon 100 may be rotated by 150 degrees on either side. In the same time the lower half shell 104 may be rotated by 30 degrees on either side. This allows a 180 degree opening of the cocoon tilted by 30 degrees towards the side of access, thus allowing access to the patient and the survival unit below the patient bed from both sides.

In one embodiment, the base support 102 of the transportation system comprises a motorized gear box configured to rotate the lower shell and/or the upper shell of the protective cocoon around their common axis by sliding over the base 102. Preferably, the gear box is configured to rotate each half shell independently from the other.

Figure 23:
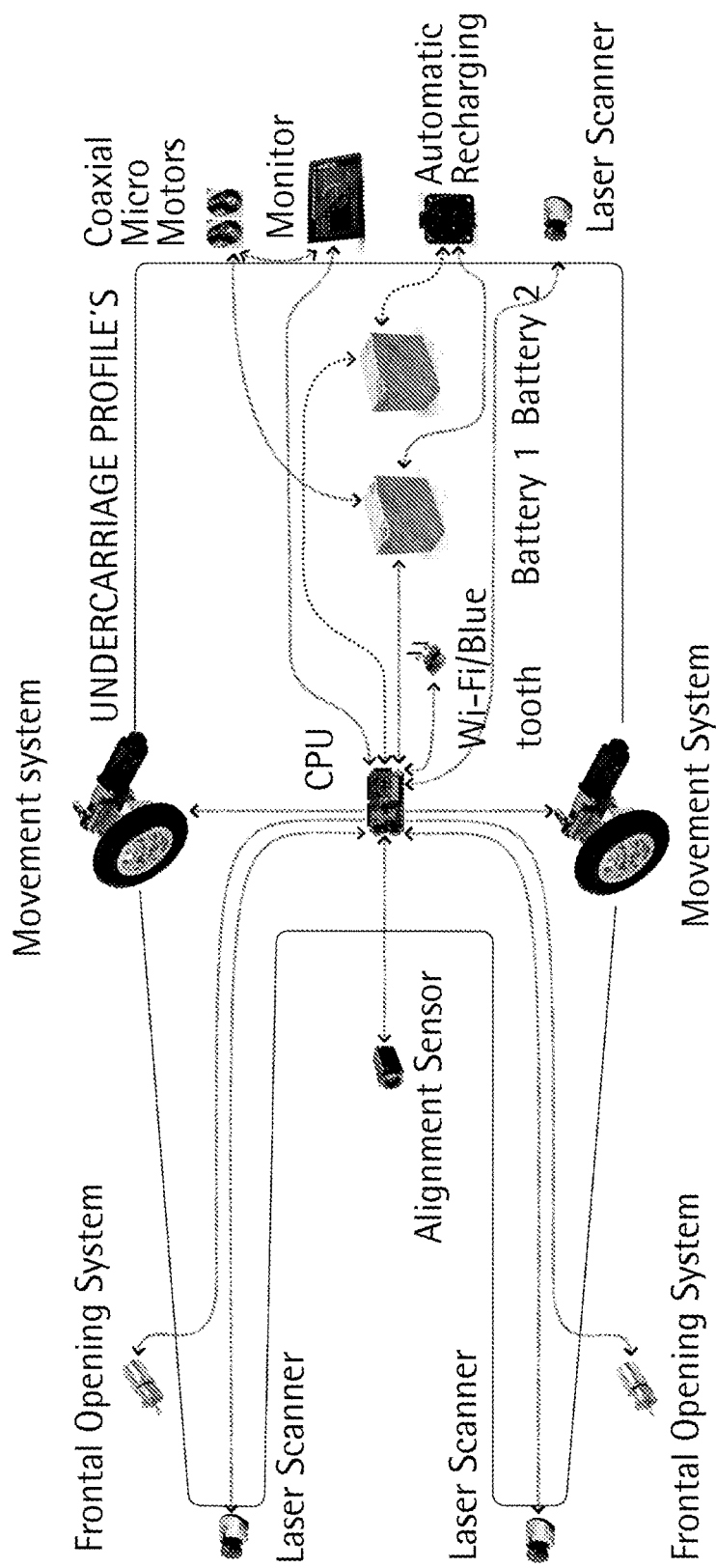
FIG. 23 is a pictorial scheme of the actuators/appliances installed in the patient transportation system according to an embodiment of the present disclosure.

The appliances installed in a robotic patient transportation system according to an embodiment of this disclosure are pictorially indicated in FIG. 23. It comprises laser scanners for detecting obstacles, a laser alignment sensor for guiding the patient transportation system to a desired position, electric motors powered by electric accumulators and driven by a CPU communicating with a remote control console through a Wi-Fi/Bluetooth communication interface. Optionally, the patient transportation system may be equipped with a touchscreen display for providing commands and with an electric socket for powering the electronic circuits installed onboard and recharging the accumulators.

By summarizing, embodiments of the present disclosure provide a patient transportation and life support system comprising a robotic movement system; a detachable surgical table system; a detachable modular life support system; and a detachable protective cocoon.

In one embodiment of the present disclosure, the embodiment comprises four main elements; i) the robotic movement system; ii) the surgical table; iii) the modular life support system; and iv) the protective cocoon with environmental control function.

The robotic movement system comprises a guidance and control system, a drive system comprising one or more drive wheels and one or more steering wheels for propelling and steering the system to and from its destination and a mechanism for reversibly attaching the surgical table, modular life support system and protective cocoon. The robotic movement system may further comprise one or more batteries to provide power to the guidance and control system and drive system. The batteries may be rechargeable.

The drive system may comprise an electric motor for rotating the drive wheel(s) at the desired speed. The movements of the robotic movement system are controlled by the guidance and control system. The guidance and control system may be remotely controlled by an operator, for example by means of radio control. The guidance and control system may also be pre-programmed, thereby allowing for the automatic movement through the hospital. Pre-programming may be done, for example, on a keypad located on the robotic movement system or remotely on a computer that controls the movement of one or more robotic movement systems.

The robotic movement system may further comprise one or more collision prevention systems, emergency brakes, emergency shut off switches and the like. The robotic movement system may further comprise a lifting or transfer system to move the surgical table together with the modular life support system onto another mobile or stationary docking point.

The surgical table is adjustable into a variety of patient positions needed for administration of anesthesia and surgery. The adjustments may be made manually or automatically by a microprocessor controlling a system of mechanical actuators. The microprocessor may be remotely controlled. The surgical table may further comprise a padding system which adapts to the patient's physiognomy and allows optimal distribution of pressure. The surgical table may remain attached to the transportation unit during surgery or alternatively may be detached and attached to a separate docking unit for the surgery. In either alternative the surgical table may also be connected with any surgical robots in the operating room and in all instances will stay underneath the patient for the entire operation and for the transportation back to the Surgical Intensive Care Unit and/or post-operative unit.

The modular life support system comprises a box containing control systems, a computer dedicated to maintaining the patient's vitals and supplies for keeping the patient under anesthesia and in good medical condition. The modular support system may further comprise several perfusions to deliver intravenous liquids to the patient. The modular life support system may further comprise an anesthetic gases system with buffer tanks and a modular connection to main gas delivery lines. The main gases include air, oxygen, nitrogen and nitrous oxide as well as vacuum. The gases can be accessed through outside connectors and are further connected to an anesthesia machine inside the modular life support system.

The modular life support system may further comprise a computer controlling sensors and actuators on the patient and the delivery of gases and liquids to the patient. The computer will allow display of information and adjustment of values. Typical sensors and actuators include, but are not limited to, sensors for measuring blood pressure, heartbeat, temperature and the like, electrocardiogram sensors, defibrillator pads and/or other muscle-stimulating electric activators to support comfort and life functions of the patient. The computer(s) may further include display elements as indicated for a particular sensor, actuator or other procedure.

The modular life support system may further comprise a suction machine.

The modular life support system further comprises additional storage for anesthetic gases and one or more batteries so that its various components can operate without being connected to the buildings main supplies, for example during transport of the patient to and from the operating room or during stand by. The batteries may be rechargeable. Nonetheless, the battery and anesthetic gases in the modular life support unit may not be sufficient for longer durations like 8 hours surgery. For this, the modular life support system has one or more docking ports for anesthetic gases and electricity. The docking ports may be included in its mechanical connection. The mechanical fixing and the media connection may be combined in a docking port. This docking port can be a fixed column e.g. arranged on the floor in the operation room or intensive care unit, delivering gases and electricity from the buildings main supplies, when the modular life support together with the surgical table are connected.

The fixed column, in turn, may further comprise a mechanism for adjusting the height and angle of the surgical table into the desired configuration for the surgery.

The protective cocoon is fixed to the robotic movement system or the surgical table and forms an envelope around the patient while the patient is moved or is in stand-by position. The protective cocoon may be made of any transparent material that is impermeable to pathogens typically found in non-sterile hospital or patient transport environments. The protective cocoon further comprises an opening mechanism to permit placement of the patient onto the patient table and/or transfer of the patient table onto different docking points. The opening mechanism may comprise a hinge and latch system or alternatively, the protective cocoon may be retractable. In either instance the opening mechanism may be manual or powered. The protective cocoon may further comprise an additional opening system which allows rapid, direct access to the patient in case of emergency. The protective cocoon may further comprise an environmental control system that maintains a minimal sterile atmosphere and aggravates the intrusion of bacteria and other contagious matter from outside. The environmental control system may be incorporated into the modular life support system or may comprise a separate unit.

The patient transportation and life support system may further comprise all necessary systems for high intensive care clinic to clinic transportation with land, sea or air transport.

Embodiments

Various embodiments of the patient transportation and life support system of the present disclosure may be the following ones:

A1. A patient transportation and life support system comprising:
a robotic movement system; and
a detachable surgical table; a detachable modular life support system; and a detachable protective cocoon.

A2. The patient transportation and life support system according to embodiment A1 wherein the robotic movement system comprises a guidance and control system, a drive system, and a mechanism for attaching the surgical table.

A3. The patient transportation and life support system according to embodiment A1 wherein the modular life support system is attached to the surgical table.

A4. The patient transportation and life support system according to embodiment A1 wherein the modular life support system is attached to the robotic movement system.

A5. The patient transportation and life support system according to embodiment A1 wherein the modular life support system comprises an anesthesia machine and one or more control systems dedicated to dedicated to monitoring and maintaining the patient's vitals and keeping the patient under anesthesia during surgery and transportation to and from the operating room.

A6. The patient transportation and life support system according to embodiment A5 wherein the modular life support system further comprises one or more perfusions.

A7. The patient transportation and life support system according to embodiment A5 wherein the modular life support system further comprises a suction machine.

A8. The patient transportation and life support system according to embodiment A5 wherein the modular life support system further comprises storage for anesthetic gases.

A9. The patient transportation and life support system according to embodiment A5 wherein the modular life support system further comprises one or more batteries.

A10. The patient transportation and life support system according to embodiment A5 wherein the control systems comprise one or more computers.

B1. A patient transportation system, comprising:
a robotic movement system including a motorized trolley and a substantially horizontal fork-shaped support having two substantially parallel cantilever beams separated by a gap; and
a protective cocoon having a substantially cylindrical shape and defining an enclosed tubular space adapted to house a patient laying on a supporting surface, the cocoon comprising:
a lower shell (104) having a substantially half-cylinder shape with an opening in correspondence of the gap of the fork-shaped support,
an upper shell (106) having a substantially half-cylinder shape coaxially hinged to said lower shell (104) so as to slide over the lower shell (104) by rotating around their common axis, the upper shell (106) being adapted to form with the lower shell (104) a tubular space having only an opening at one end through which a supporting surface with a patient laying thereon may be inserted,
a base support (102) adapted to be laid upon the fork-shaped support and to sustain said lower shell (104), defining a substantially cylindrical surface having a bottom hatch in correspondence of the gap of the fork-shaped support, and
at least one door hinged to said base support (102) and adapted to close said opening of the tubular space.

B2. The patient transportation system of embodiment B1, comprising two half-circular doors hinged to said base support (102) and adapted to close said opening of the tubular space.

B3. The patient transportation system of embodiment B1, further comprising clamping means installed in said tubular space, for attaching said supporting surface with a patient laying thereon.

B4. The patient transportation system of embodiment B3, wherein said clamping means are mechanically coupled to electric linear actuators fixed to said fork-shaped support and configured to lift a patient's supporting surface attached to said clamping means.

B5. The patient transportation system of embodiment B1, wherein the robotic movement system comprises an electric motor for moving the patient transportation system, electric accumulators coupled to power said electric motor and a control system configured to command said electric motor.

B6. The patient transportation system of embodiment B5, further comprising a laser guidance system.

B7. The patient transportation system of embodiment B1, wherein said base support comprises motorized arms configured to sustain laterally said lower shell and to rotate the lower shell around its axis by sliding over said base.

B8. The patient transportation system of embodiment B1, wherein said base support comprises a motorized gear box configured to rotate the lower shell and the upper shell around their common axis by sliding over said base.

B9. The patient transportation system of embodiment B1, further comprising a detachable modular life support system comprising an anesthesia machine and one or more control systems dedicated to dedicated to monitoring and maintaining the patient's vitals and keeping the patient under anesthesia during surgery and transportation to and from the operating room.

B10. The patient transportation system of embodiment B3, comprising a supporting surface configured to be attached/detached to said clamping means, said supporting surface being configured to be placed upon and firmly connected to a ground post and to be sustained thereby.

C1. A patient holding hospital unit, said unit comprising:
a supporting surface configured to receive a patient; and
a life support system restrained to said supporting surface, said system comprising:
an anesthesia machine;
a plurality of reservoirs suitable to contain gases under pressure;
a first set of gas supply ducts respectively connected to outlet ports of said reservoirs, the free ends of said gas supply ducts being provided with respective dispensing valves;
a second set of gas supply ducts respectively connected to inlet ports of said reservoirs, the free ends of said gas supply ducts being provided with respective supply valves;
one or more perfusion devices;
an automatic control system operably connected to said anesthesia machine, dispensing valves, perfusion devices and provided with a control interface;
a power supply unit operably connected to said automatic control system; and
a power supply line operably connected to said automatic control system in parallel relative to said power supply unit, said power supply line having an electric connector,
wherein said anesthesia machine, reservoirs and related ducts, perfusion devices, automatic control system, power supply unit and power supply line are arranged in a container restrained to said patient supporting surface, and
wherein the dispensing valves are arranged on an external surface of said container together with said control interface and said supply valves and electric connector of the power supply line are arranged at a connecting member adapted to be mounted to a base member configured to supply gases under pressure to the reservoirs and power to the control system.

C2. A patient holding hospital unit according to embodiment C1, wherein said life support system is further equipped with a computerized system configured to monitor, to control and to adapt functions performed by the appliances of the life support system in order to preserve patient's vital functions.

C3. A patient holding hospital unit according to embodiment C1, wherein said unit further comprises a protective cocoon-shaped container, said container being configured to house said patient supporting surface and a life support system.

C4. A patient holding hospital unit according to embodiment C3, wherein said cocoon-shaped container is a substantially cylindrical shell comprising:
a lower shell (104) having a substantially half-cylinder shape with a central longitudinal opening,
an upper shell (106) having a substantially half-cylinder shape coaxially hinged to said lower shell (104) so as to slide over the lower shell (104) by rotating around their common axis, the upper shell (106) being adapted to form with the lower shell (104) a tubular space having only an opening at one end through which a supporting surface with a patient laying thereon may be inserted,
a base support (102) adapted to support said lower shell (104), and
at least one door hinged to said base support (102) and adapted to close said opening of the tubular space.

C5. A patient holding hospital unit according to embodiment C4, further comprising a trolley, said cocoon-shaped container being restrained to said trolley.

C6. A patient holding hospital unit according to embodiment C5, wherein said trolley includes a substantially horizontal fork-shaped frame having two substantially parallel cantilever beams separated by a gap, said cocoon-shaped container being mounted on said beams and the central longitudinal opening of the lower shell being arranged at the gap between the beams.

C7. A patient holding hospital unit according to embodiment C5 or C6, wherein said trolley comprises a robotic movement system configured to automatically drive the trolley.

C8. A patient holding hospital unit according to embodiment C7, wherein the robotic movement system comprises an electric motor operably coupled to trolley wheels, electric accumulators coupled to power said electric motor and a control system configured to command said electric motor.

C9. A patient holding hospital unit according to embodiment C8, further comprising a laser guidance system.

D1. A patient holding hospital system, comprising:
a surgical table defining a patient supporting surface and having fasteners of a first set installed on the opposite side of said patient supporting surface;
a T-shaped connecting member having:
a top portion having fasteners of a second set adapted to engage in a detachable manner with the fasteners of the first set to hold firmly the surgical table,
a bottom portion having fasteners and connectors of a third set adapted to engage in a detachable manner with upper fasteners and connectors of a mount of a surgical station and to keep firmly the T-shaped connecting member to the mount,
at least one side portion having fasteners and connectors of a fourth set, and
internal conduits and at least an electric cable joining together corresponding connectors of the third set and of the fourth set; and
a life support system, having:
holding fasteners adapted to engage in a detachable manner with the fasteners of the fourth set and to keep firmly the life support system to the T-shaped connecting member,
inlet gas connectors and at least an input electric connector configured to couple in a detachable manner with corresponding connectors of the fourth set,
outlet gas connectors adapted to couple with external tubes for delivering oxygen and/or an anesthetic gas, and
electrically operated devices for supporting life of a patient laying on the surgical table, configured to be powered through said input electric connector and having inlet gas conduits coupled with the inlet gas connectors and outlet gas conduits coupled with the outlet gas connectors.

D2. The patient holding hospital system of embodiment D1, wherein said T-shaped connecting member further comprises a second side portion having fasteners and connectors of a fifth set and internal conduits and at least an electric cable joining together corresponding connectors of the third set and of the fifth set.

D3. The patient holding hospital system of embodiment D1, wherein said surgical table is composed of a plurality of rigid parts hinged together.

D4. The patient holding hospital system of embodiment D1, wherein said life support system comprises gas tanks coupled with said inlet and outlet gas conduits.

E1. A patient transportation and life support system, comprising the patient holding hospital system of one of the embodiments from D1 to D4 and the patient transportation system of one of the embodiments from B1 to B10.

It is understood that the foregoing detailed description is merely illustrative and is not to be taken as a limitation upon the scope according to an embodiment of the present disclosure, which is defined solely by the appended claims and their equivalents. Various changes and modifications to the disclosed embodiments will be apparent to those skilled in the art.

The invention claimed is:

1. A patient holding hospital unit, comprising:
a supporting surface configured to receive a patient; and
a life support system restrained to said supporting surface, said system comprising:
   an anesthesia machine;
   a plurality of reservoirs adapted to contain gases under pressure;
   a first set of gas supply ducts respectively connected to outlet ports of said reservoirs, free ends of said gas supply ducts being provided with respective dispensing valves;
   a second set of gas supply ducts respectively connected to inlet ports of said reservoirs, free ends of said second set of gas supply ducts being provided with respective supply valves;
   one or more perfusion devices;
   an automatic control system operably connected to said anesthesia machine, dispensing valves, perfusion devices and provided with a control interface;
   a power supply unit operably connected to said automatic control system; and
   a power supply line operably connected to said automatic control system in parallel relative to said power supply unit, said power supply line having an electric connector,
wherein said anesthesia machine, reservoirs and related ducts, perfusion devices, automatic control system, power supply unit and power supply line are arranged in a container restrained to said patient supporting surface,
wherein the dispensing valves are arranged on an external surface of said container together with said control interface and said supply valves and electric connector of the power supply line are arranged at a connecting member adapted to be mounted to a base member configured to supply gases under pressure to the reservoirs and power to the control system, and wherein said connecting member is a T-shaped connecting member having:
a top portion having fasteners of a second set adapted to engage in a detachable manner with fasteners of a first set of a surgical table, to hold firmly said surgical table,
a bottom portion having fasteners and connectors of a third set adapted to engage in a detachable manner with upper fasteners and connectors of a mount of a surgical station and to keep the T-shaped connecting member firmly connected to the mount,
at least one side portion having fasteners and connectors of a fourth set,
   internal conduits and at least an electric cable joining together corresponding connectors of the third set and of the fourth set, and
wherein said life support system further comprises:
   holding fasteners adapted to engage in a detachable manner with the fasteners of the fourth set and to keep the life support system firmly connected to the T-shaped connecting member,
   inlet gas connectors and at least an input electric connector configured to couple in a detachable manner with corresponding connectors of the fourth set,
   outlet gas connectors adapted to couple with external tubes for delivering oxygen and/or an anesthetic gas, and
   electrically operated devices for supporting life of a patient laying on the surgical table, configured to be powered through said input electric connector and having inlet gas conduits coupled with the inlet gas connectors and outlet gas conduits coupled with the outlet gas connectors.

2. The patient holding hospital unit according to claim 1, wherein said life support system is further equipped with a computerized system configured to monitor, to control and to adapt functions performed by appliances of the life support system in order to preserve the patient's vital functions.

3. The patient holding hospital unit according to claim 1, wherein said unit further comprises a protective cocoon-shaped container, said container being configured to house said patient supporting surface and said life support system.

4. The patient holding hospital unit according to claim 3, wherein said cocoon-shaped container is a substantially cylindrical shell comprising:
a lower shell having a substantially half-cylinder shape with a central longitudinal opening,
an upper shell having a substantially half-cylinder shape coaxially hinged to said lower shell so as to slide over the lower shell by rotating around a central axis of symmetry of the lower shell, the upper shell being adapted to form with the lower shell a tubular space having only an opening at one end through which a supporting surface with a patient laying thereon may be inserted,
a base support adapted to support said lower shell, and
at least one door hinged to said base support and adapted to close said opening of the tubular space.

5. The patient holding hospital unit according to claim 4, further comprising a trolley, said cocoon-shaped container being restrained to said trolley.

6. The patient holding hospital unit according to claim 5, wherein said trolley includes a substantially horizontal fork-shaped frame having two substantially parallel cantilever beams separated by a gap, said cocoon-shaped container being mounted on said cantilever beams and the central longitudinal opening of the lower shell being arranged at the gap between the beams.

7. The patient holding hospital unit according to claim 5, wherein said trolley comprises a robotic movement system configured to automatically drive the trolley.

8. The patient holding hospital unit according to claim 7, wherein the robotic movement system comprises an electric motor operably coupled to trolley wheels, electric accumulators coupled to power said electric motor and a control system configured to command said electric motor.

9. The patient holding hospital unit according to claim 8, further comprising a laser guidance system.

10. The patient holding hospital unit of claim 1, wherein said T-shaped connecting member further comprises a second side portion having fasteners and connectors of a fifth set and internal conduits and at least an electric cable joining together corresponding connectors of the third set and of the fifth set.

11. The patient holding hospital unit of claim 1, wherein said supporting surface is composed of a plurality of rigid parts hinged together.

12. A patient transportation and life support system, comprising:
   a robotic movement system including a motorized trolley and a substantially horizontal fork-shaped support having two substantially parallel cantilever beams separated by a gap, and
   a protective cocoon having a substantially cylindrical shape and defining an enclosed tubular space adapted to house a patient laying on a supporting surface, the cocoon comprising:
      a lower shell having a substantially half-cylinder shape with an opening in correspondence of the gap of the fork-shaped support,
      an upper shell having a substantially half-cylinder shape coaxially hinged to said lower shell so as to slide over the lower shell by rotating around a central axis of symmetry of the lower shell, the upper shell being adapted to form with the lower shell a tubular space having only an opening at one end through which a supporting surface with a patient laying thereon may be inserted,
      a base support adapted to be laid upon the fork-shaped support and to sustain said lower shell, defining a substantially cylindrical surface having a bottom hatch in correspondence of the gap of the fork-shaped support,
      at least one door hinged to said base support and adapted to close said opening of the tubular space, and
   the patient holding hospital unit of claim 1.

13. The patient transportation and life support system of claim 12, comprising two half-circular doors hinged to said base support and adapted to close said opening of the tubular space.

14. The patient transportation and life support system of claim 12, further comprising clamping means installed in said tubular space, for attaching to said supporting surface.

15. The patient transportation and life support system of claim 14, wherein said clamping means are mechanically coupled to electric linear actuators fixed to said fork-shaped support and configured to lift a patient's supporting surface attached to said clamping means.

16. The patient transportation and life support system of claim 12,
   wherein the robotic movement system comprises an electric motor for moving the patient transportation and life support system, electric accumulators coupled to power said electric motor and a control system configured to command said electric motor.

17. The patient transportation and life support system of claim 16, further comprising a laser guidance system.

18. The patient transportation and life support system of claim 12,
   wherein said base support comprises motorized arms configured to sustain laterally said lower shell and to rotate the lower shell around said central axis of symmetry by sliding over said base support.

19. The patient transportation and life support system of claim 12,
   wherein said base support comprises a motorized gear box configured to rotate the lower shell and the upper shell around a common axis by sliding over said base support.

* * * * *